US00PP08878P

United States Patent [19]

Kordes

[11] Patent Number: Plant 8,878

[45] Date of Patent: Sep. 6, 1994

[54] SHRUB ROSE PLANT NAMED KORADES

[75] Inventor: Wilhelm Kordes, Sparrieshoop, Fed. Rep. of Germany

[73] Assignee: Bear Creek Gardens, Inc., Medford, Oreg.

[21] Appl. No.: 126,216

[22] Filed: Sep. 22, 1993

[51] Int. Cl.[5] ..... A01H 5/00

[52] U.S. Cl. ..... Plt./1

[58] Field of Search ..... Plt. 1, 26, 27, 28

*Primary Examiner*—Howard J. Locker

*Attorney, Agent, or Firm*—Klarquist Sparkman Campbell Leigh & Whinston

[57] ABSTRACT

A shrub rose having a vigorous, well-branched and upright habit of growth; dark green, glossy, disease-resistant foliage and attractive pink flowers; and being easily propagated from softwood cuttings.

1 Drawing Sheet

The present invention relates to a new and distinct variety of rose plant of the shrub class which was originated by me by crossing the variety KORmarie with an unnamed seedling.

The primary objective of this breeding was to produce a new rose variety having the shrub-like characteristics and healthy foliage of KORmarie combined with the very healthy foliage of the unnamed seedling. Flower color could be anything between the yellow-pink flowers of KORmarie and the red of the unnamed seedling. The objective was substantially achieved, along with other desirable improvements, as evidenced by the following unique combination of characteristics that are outstanding in the new variety and that distinguish it from its parents, as well as from all other varieties of which I am aware:

1. A vigorous, upright, well-branched growth habit;
2. Dark green, glossy and healthy foliage;
3. Dark pink, lightly scented flowers; and
4. Ease of propagation from softwood cuttings.

Asexual reproduction of this new variety by softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORmarie.

*Pollen parent.*—Unnamed seedling.

Classification:

*Botanical.*—*Rosa hybrida.*

*Commercial.*—Shrub.

FLOWER

Observations made from specimens grown in garden environments in Somis, Calif., and Sparrieshoop, Germany.

Blooming habit: Continuous.

Bud:

*Size.*—1 inch in length when the petals start to unfurl.

*Form.*—Short, globular.

*Color.*—When sepals first divide, bud color is Red Group 52A. When half blown, the upper and lower sides of the petals are Red Group 52A.

*Sepals.*—Color: Green Group 138C. Surface texture: Covered in fine hairs. There are three lightly appendaged sepals. There are two unappendaged sepals with hairy edges.

*Receptacle.*—Color: Green Group 137D. Shape: Apple. Size: Medium ($\frac{3}{8}$ inch$\times\frac{3}{8}$ inch). Surface: Glandular.

*Peduncle.*—Length: Short ($1\frac{1}{2}$ to 2 inches). Surface: Glandular. Color: Light green. Stength: Bending, slender.

Bloom:

*Size.*—Medium. Average open size is 3 inches in diameter.

*Borne.*—Several together in pyramidal clusters of 3 to 15 flowers.

*Stems.*—Medium (18 inches), strong.

*Form.*—Cupped when first open. Permanence: Retains its form to the end.

*Petalage.*—Number of petals under normal conditions: 20 to 25.

*Color.*—The upper and lower sides of the petals are Red Group 52A. The base of each petal has a small, White Group 155A half moon at the point of attachment. The major color on the upper side is Red Group 52A.

*Variegations.*—None.

*Discoloration.*—The general tonality at the end of the first day and third days: No change.

*Fragrance.*—Moderate.

Petals:

*Texture.*—Thin.

*Shape.*—Oval.

*Form.*—Cupped.

*Arrangement.*—Imbricated, with few petaloids in the center.

*Persistence.*—Drop off cleanly.

*Lastingness.*—On the plant: Short (3 to 4 days). As a cut flower: Short (3days).

Reproductive parts:

*Anthers.*—Size: Medium. Quantity: Many. Color: Yellow. Arrangement: Regular around styles.

*Filaments.*—Color: White.

*Pollen.*—Color: Gold-yellow.

*Styles.*—Color: White.

*Stigmas.*—Color: Yellow.

Form: Bush.

Growth: Vigorous, upright, well-branched shrub to 5 feet in height and 4 feet in length at 2 years of age.

Foliage:

*Number of leaflets on normal mid-stem leaves.*—5 to 7.

*Size.*—Largee (6½ inches×4½ inches.

*Quantity.*—Normal.

*Color.*—New foliage: Green Group 137B. Old foliage: Green Group 139A.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish when young and then becoming green.

*Petiole underside.*—Rough with prickles and glands.

*Stipules.*—Medium (½ inch), bearded.

*Disease resistance.*—Resistant to mildew and rust under normal growing conditions at Somis, Calif., and Sparrieshoop, Germany.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium (¼ inch), straight to hooked slightly downward.

*Color when young.*—Red.

Small prickles:

*Quantity.*—Many on main stalks. Many on laterals.

*Color.*—Brown.

I claim:

1. A new and distinct variety of rose plant of the shrub class, substantially as herein shown and described, characterized particularly as to novelty by the unique combination of its vigorous, well-branched and upright habit of growth; its dark green, glossy and disease resistant foliage; its attractive pink flowers and its ease of propagation from softwood cuttings.

* * * * *

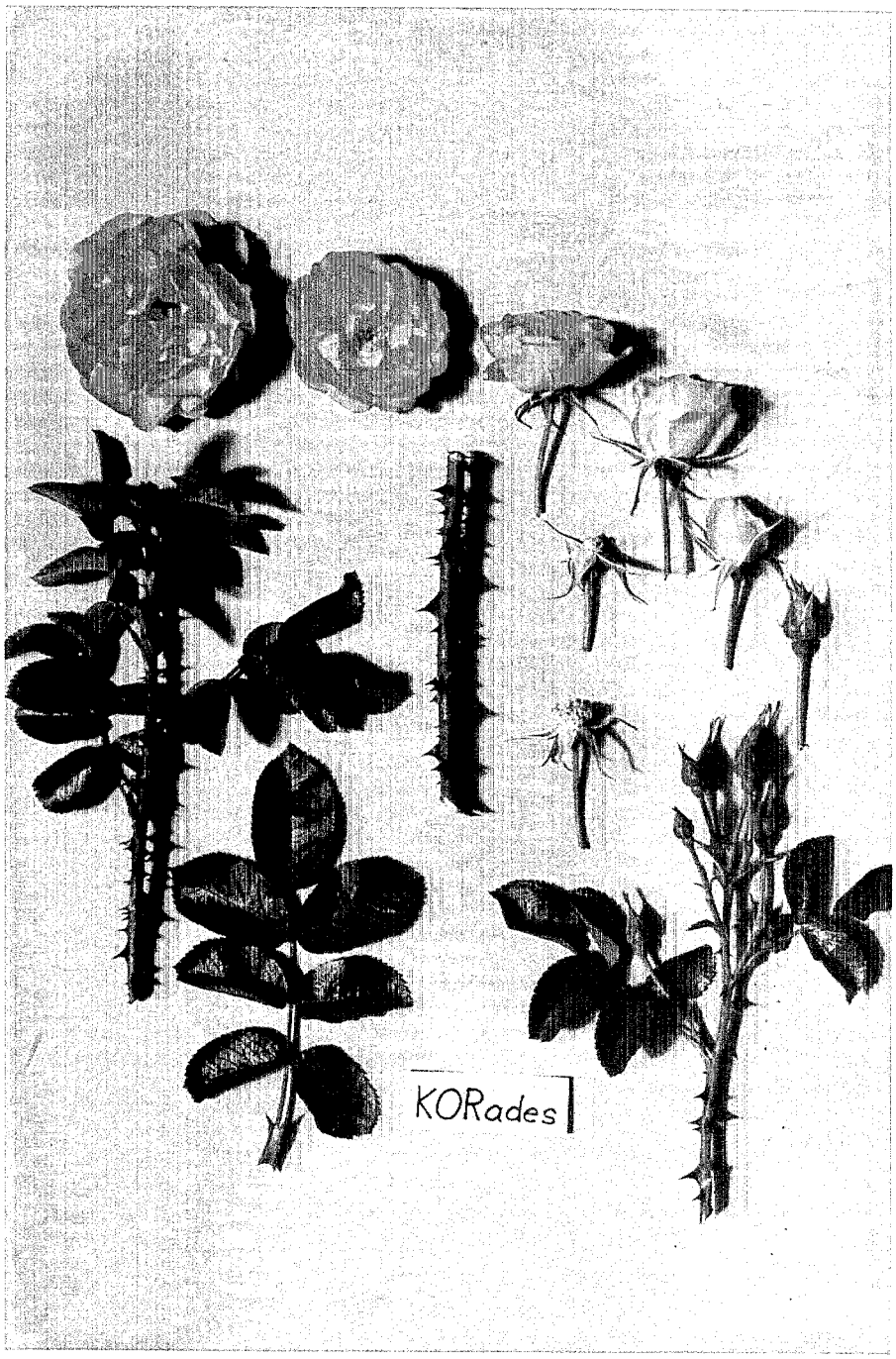
KORades